United States Patent
Myung et al.

(10) Patent No.: US 10,420,728 B2
(45) Date of Patent: Sep. 24, 2019

(54) TABLET AND METHOD OF PREPARING THE SAME

(71) Applicant: Boryung Pharmaceutical Co., Ltd, Seoul (KR)

(72) Inventors: Jayhyuk Myung, Seoul (KR); Sung Chan Jeong, Gyeonggi-do (KR); Yun Sam Kim, Gyeonggi-do (KR)

(73) Assignee: Boryung Pharmaceutical Co., Ltd., Seoul (KR)

( * ) Notice: Subject to any disclaimer, the term of this patent is extended or adjusted under 35 U.S.C. 154(b) by 0 days.

(21) Appl. No.: 15/548,754

(22) PCT Filed: Jan. 11, 2016

(86) PCT No.: PCT/KR2016/000221
§ 371 (c)(1),
(2) Date: Aug. 3, 2017

(87) PCT Pub. No.: WO2016/126012
PCT Pub. Date: Aug. 11, 2016

(65) Prior Publication Data
US 2018/0015043 A1  Jan. 18, 2018

(30) Foreign Application Priority Data

Feb. 5, 2015  (KR) .................. 10-2015-0018182
Jul. 20, 2015  (CN) .................. 2015 1 0426945

(51) Int. Cl.
*A61J 3/00* (2006.01)
*A61J 3/10* (2006.01)
(Continued)

(52) U.S. Cl.
CPC ............ *A61K 9/2095* (2013.01); *A61J 3/007* (2013.01); *A61J 3/10* (2013.01); *A61K 9/2018* (2013.01);
(Continued)

(58) Field of Classification Search
None
See application file for complete search history.

(56) References Cited

U.S. PATENT DOCUMENTS

2015/0147394 A1* 5/2015 Kim .................... A61K 9/2018
424/474

FOREIGN PATENT DOCUMENTS

CA  2877444 A1  1/2014
CA  2887056 A1  4/2014
(Continued)

OTHER PUBLICATIONS

Omelczuk et al., "Influence of micronization on the compaction properties of an investigational drug using tableting index analysis"; European Journal of Pharmaceutics and Biopharmaceutics 43; 1997, pp. 95-100.

(Continued)

*Primary Examiner* — Aradhana Sasan
(74) *Attorney, Agent, or Firm* — Greenberg Traurig, LLP (57) ABSTRACT

Disclosed is a method for preparing a tablet. The method can improve the compressibility of the active ingredients and produce tablets of uniform quality, bringing about the advantage of increasing tablet hardness with an increase in compression pressure, easily controlling disintegration time, and decreasing tablet friability by using the active ingredient fimasartan, a pharmaceutically acceptable salt thereof or a hydrate or solvate thereof having a specific particle size distribution.

20 Claims, 1 Drawing Sheet

(51) Int. Cl.
  *A61K 9/20* (2006.01)
  *A61K 9/28* (2006.01)
  *A61K 31/506* (2006.01)
  *A61K 31/513* (2006.01)
(52) U.S. Cl.
  CPC ............ *A61K 9/2054* (2013.01); *A61K 9/284* (2013.01); *A61K 31/506* (2013.01); *A61K 31/513* (2013.01); *A61K 9/2866* (2013.01)

(56) References Cited

FOREIGN PATENT DOCUMENTS

| | | |
|---|---|---|
| CN | 103446069 A | 12/2013 |
| CN | 103655539 A | 3/2014 |
| EA | 200900646 A1 | 5/1999 |
| JP | 2012153631 A | 8/2012 |
| KR | 20040097996 A | 11/2004 |
| KR | 20050062467 A | 6/2005 |
| KR | 20130100237 A | 9/2013 |
| KR | 20130130028 A | 11/2013 |
| KR | 2014/0113512 A | 9/2014 |
| KR | 20150008513 A | 1/2015 |
| RU | 2130310 C1 | 5/1999 |
| WO | 2007/131930 A1 | 11/2007 |
| WO | 2012/14385 A1 | 10/2012 |
| WO | 2014/003305 A1 | 1/2014 |
| WO | 2014/058268 A1 | 4/2014 |
| WO | 2017/058268 A1 | 4/2014 |

OTHER PUBLICATIONS

Akbarieh et al., "Morphic features of solid particles after micronization in the fluid energy mill"; International Journal of Pharmaceutics, 35; 1987, pp. 81-89.

Zheng et al., "A Survey of Pharmaceutical Powder Tabletability"; Progress in Pharmaceutical Sciences, Mar. 30, 2006, vol. 30, No. 3.

Wang et al., "Recent updates of studies on powder characterization", Chinese Journal of New Drugs 2006, vol. 15 No. 18, pp. 1535-1539.

Hulling et al., Pharmaceuticals, Feb. 28, 2014, pp. 173.

Zhu et al., Research on the correlation between physical properties of materials and table molding, Chinese Traditional Patent Medicine, Aug. 2010, vol. 32 No. 8, pp. 1402-1404.

Wang et al., "Factors affecting pharmaceutical powder tabletability and strategies for improvement", Chinese Pharmaceutical Journal, vol. 48 No. 11, Jun. 2013, pp. 845-849.

* cited by examiner

TABLET AND METHOD OF PREPARING THE SAME

CROSS-REFERENCE

This application is a 371 National Phase Application of International Application No. PCT/KR2016/000221, filed Jan. 11, 2016, which claims priority to CN Patent Application Serial No. 201510426945.4, filed on Jul. 20, 2015, and KR Patent Application Serial No. 10-2015-0018182, filed Feb. 5, 2015, the contents of which are all incorporated by reference in their entireties.

TECHNICAL FIELD

The present invention relates to a tablet comprising fimasartan, a pharmaceutically acceptable salt thereof, or a hydrate or solvate thereof as an active ingredient, and a method for preparing the same.

More particularly, the present invention relates to a tablet superior in terms of hardness and friability where an active ingredient particle with a small diameter is used to improve tableting characteristics, and a method for preparing the same.

BACKGROUND ART

Fimasartan is angiotensin II receptor antagonist used for the treatment of hypertension, and is commercially available in doses of 30 mg, 60 mg and 120 mg under the brand name of Kanarb, which is in the form of fimasartan potassium trihydrate.

As disclosed in Korean Patent Application Publication No. 10-2004-0032639, fimasartan can be used in the form of fimasartan potassium trihydrate.

However, when synthesized fimasartan potassium trihydrate is used for the mass production of tablets, the tablets has the difference in physical properties from one to another to deteriorate the tablet quality. In addition, the synthesized fimasartan potassium trihydrate is unlikely to be compressed even at a high compression pressure, so that the tablets exhibit poor hardness and friability.

There is therefore a need for a tablet of fimasartan potassium trihydrate that is uniform in quality and superior in terms of hardness and friability, and a method for preparing the same.

PRIOR ART DOCUMENT

Patent Document

Korean Patent Application Publication No. 10-2004-0032639

DISCLOSURE OF INVENTION

Technical Problem

It is an object of the present invention to provide a method for preparing a tablet comprising fimasartan, a pharmaceutically acceptable salt thereof, or a hydrate or solvate thereof.

It is another object of the present invention to provide a tablet comprising fimasartan, a pharmaceutically acceptable salt thereof, or a hydrate or solvate thereof.

Solution to Problem

The present invention provides a method for preparing a tablet comprising fimasartan, a pharmaceutically acceptable salt thereof, or a hydrate or solvate thereof as an active ingredient, the method comprising milling the active ingredient to allow 50% (v/v) of the active ingredient based on the total amount of the active ingredient contained in the tablet to have a diameter of 10 µm or less.

In the tablet comprising fimasartan, a pharmaceutically acceptable salt thereof, or a hydrate or solvate thereof as the active ingredient according to the present invention, the active ingredient is milled such that 50% (v/v) of the active ingredient based on the total amount of the active ingredient has a diameter of 10 µm or less. Given the particle size distribution, the active ingredient particles can be of high compressibility so that they can be more greatly compressed according to an increase in compression pressure, which makes it possible to easily control the hardness and disintegration time of the tablet and to decrease the friability of the tablet. In addition, even when manufactured on a mass scale, tablets comprising the active ingredient particles in such a particle size distribution exhibit uniform physical properties.

To the contrary, when 50% (v/v) or greater of the active ingredient based on the total amount of the active ingredient in a tablet have a diameter of greater than 10 µm, compressibility of the active ingredients is poor, making it difficult to manufacture a tablet having sufficient hardness even at a high compression pressure. With such a particle size distribution of the active ingredient particles, there is difficulty in controlling the hardness and disintegration time of the tablet and the tablet exhibits inferior friability. As a result, non-uniform physical properties are detected over the tablets manufactured on a mass scale, thus degrading the product quality.

Figure 1:
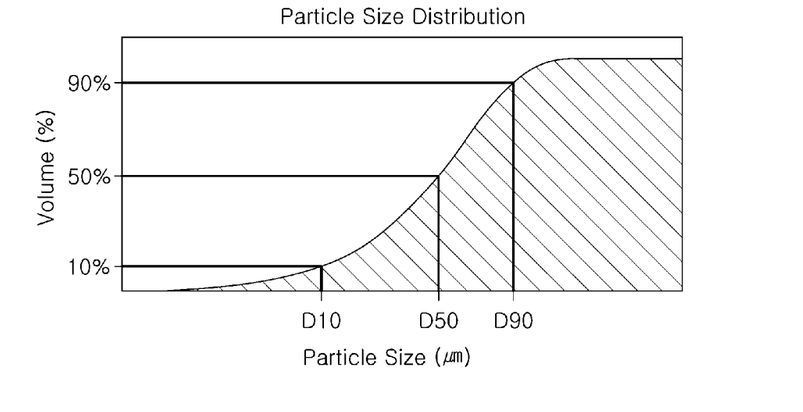
FIG. 1 is a graph of a particle size distribution illustrating definitions of D50 and D90 with regard to particle sizes.

On a particle size distribution, as depicted in FIG. 1, D50 is the value of the diameter of the active ingredient particle at 50% (v/v) of the active ingredient based on the total amount of the active ingredients in the cumulative distribution, and D90 is the value of the diameter of the active ingredient particle at 90% (v/v) of the active ingredient based on the total amount of the active ingredients in the cumulative distribution (Malvern Instruments Worldwide, 2012, A Basic Guide to Particle Characterization).

In accordance with an aspect of the present invention, the present invention provides a method for preparing a tablet, comprising:

milling at least 50% (v/v) of an active ingredient based on the total amount of the active ingredient into particles of which have a diameter of 10 µm or less, the active ingredient being fimasartan, a pharmaceutically acceptable salt thereof, or a hydrate or solvate thereof;

mixing the particles of the milled active ingredient with a pharmaceutically acceptable additive to give a mixture; and forming the tablet from the mixture.

In exemplary embodiments of the present invention, the milling step may be carried out in such a way that 50% (v/v) of the active ingredient based on the total amount of the active ingredient contained in the tablet may be milled into the particles having a diameter of 10 µm or less. In exemplary embodiments of the present invention, the milling step may be carried out in such a way that 90% (v/v) of the active ingredient based on the total amount of the active ingredient contained in the tablet may be milled into the particles having a diameter of 25 µm or less.

In exemplary embodiments of the present invention, the milling step may be carried out in such a way that 90% (v/v) of the active ingredient based on the total amount of the active ingredient contained in the tablet may be milled into the particles having a diameter of 25 µm or less, and 50%

(v/v) of the active ingredient based on the total amount of the active ingredient may be milled into the particles having a diameter of 10 µm or less. In exemplary embodiments of the present invention, the milling step may be carried out in such a way that 50% (v/v) of the active ingredient based on the total amount of the active ingredient contained in the tablet may be milled into the particles having a diameter of 6 µm or less.

In exemplary embodiments of the present invention, the milling step may be carried out in such a way that 90% (v/v) of the active ingredient based on the total amount of the active ingredient contained in the tablet may be milled into the particles having a diameter of 15 µm or less.

In exemplary embodiments of the present invention, the milling step may be carried out in such a way that 90% (v/v) of the active ingredient based on the total amount of the active ingredient contained in the tablet may be milled into the particles having a diameter of 15 µm or less, and 50% (v/v) of the active ingredient based on the total amount of the active ingredient contained in the tablet may be milled into the particles having a diameter of 6 µm or less.

In exemplary embodiments of the present invention, the milling step may be carried out in such a way that the active ingredient fimasartan, a pharmaceutically acceptable salt thereof, or a hydrate or solvate thereof is milled into the particles having a diameter of 0.5 µm or more.

In another exemplary embodiment of the present invention, the milling step may be carried out in such a way that the active ingredient fimasartan, a pharmaceutically acceptable salt thereof, or a hydrate or solvate thereof is milled into particles having a diameter of 2 µm or more, preferably 3 µm or more. When the particle of the active ingredients has the above diameter range, the active ingredient particles are easy to handle and prepare into a tablet since static electricity is less prone to occur in that diameter range.

In the tablet, the active ingredient fimasartan, a pharmaceutically acceptable salt thereof, or a hydrate or solvate thereof amounts to approximately 40 weight % or higher based on the total weight of the tablet. In this regard, the physical properties of the tablet greatly depend on those of the active ingredient. Hence, when the active ingredient is milled in the form of particles, it is possible to easily control physical properties of the tablet and to improve uniformity of the physical properties of the tablet.

When the particles of the active ingredients have the above-described size distribution, the active ingredient is highly compressible such that they can be more greatly compressed with an increase in compression pressure, which makes it possible to easily control the hardness and disintegration time of the tablet and to decrease the friability of the tablet. In addition, even when manufactured on a mass scale, tablets containing the active ingredient in such a size distribution exhibit uniform physical properties.

In one exemplary embodiment of the present invention, the tablet may include the active ingredient fimasartan, a pharmaceutically acceptable salt thereof, or a hydrate or solvate thereof in an amount of 30 weight % or more, based on the total weight of the tablet, preferably in an amount of 40 weight % to 70 weight %, and more preferably in an amount of 40 weight % to 60 weight %. In spite of a high content of the active ingredient fimasartan, a pharmaceutically acceptable salt thereof, or a hydrate or solvate thereof, hardness and disintegration time of the tablet can be easily controlled and friability of the tablet can be decreased because the active ingredient is used in the form of particles having the above particle size distribution.

In the present invention, the milling the active ingredient may be achieved using a method or an apparatus that is typically used in the medicinal and pharmaceutical field, for example, a jet mill if it does not degrade the activity of the active ingredient.

So long as it is typical in the medicinal and pharmaceutical field and does not cause a stomach disorder, allergy, dizziness, and the like when administered to humans, any pharmaceutically acceptable additive may be used in the present invention without special limitations thereto. The pharmaceutically acceptable additive may be a carrier, an excipient, a diluent, or a mixture thereof. Examples of the carrier, the excipient, or the diluent may include lactose, lactose hydrate, dextrose, sucrose, sorbitol, mannitol, xylitol, erythritol, maltitol, starch, corn starch, acacia gum, alginate, gelatin, calcium phosphate, calcium silicate, cellulose, methyl cellulose, ethyl cellulose, polyvinyl pyrrolidone, crospovidone, sodium starch glycolate, hydroxypropylcellulose, hydroxypropylmethylcellulose, hydroxyethylcellulose, methyl hydroxybenzoate, propyl hydroxybenzoate, talc, croscarmellose sodium, magnesium stearate, mineral oil, microcrystalline cellulose, or a mixture thereof, with preference for lactose, lactose hydrate, microcrystalline cellulose, croscarmellose sodium, magnesium stearate, or a mixture thereof.

According to the present invention, the forming the tablet may be performed in various manners. For example, the tablet may be manufactured using a direct compression process, or a wet or dry granulation process. Preferably, the tablet may be prepared by a wet granulation process.

In another exemplary embodiment of the present invention, the forming the tablet may comprise granulating the mixture. Granules may be prepared from the mixture, and the granules may be mixed with an additional pharmaceutically acceptable additive to give a granule-containing mixture that is then compressed into a tablet. For example, the granules may be prepared by the wet granulation process using a liquid binder. The granule may be prepared by using a high shear mixer (HSM) or fluidized bed granulator (FBG).

According to the present invention, the additional pharmaceutically acceptable additive may be a carrier, an excipient, a diluent, or a mixture thereof. Examples of the carrier, the excipient, or the diluent include lactose, lactose hydrate, dextrose, sucrose, sorbitol, mannitol, xylitol, erythritol, maltitol, starch, corn starch, acacia gum, alginate, gelatin, calcium phosphate, calcium silicate, cellulose, methyl cellulose, ethyl cellulose, microcrystalline cellulose, polyvinyl pyrrolidone, crospovidone, sodium starch glycolate, hydroxypropylcellulose, hydroxypropylmethylcellulose, hydroxyethylcellulose, methyl hydroxybenzoate, propyl hydroxybenzoate, talc, croscarmellose sodium, magnesium stearate, mineral oil, or a mixture thereof, with preference for lactose, lactose hydrate, microcrystalline cellulose, croscarmellose sodium, magnesium stearate or a mixture thereof. More preferred is magnesium stearate.

In exemplary embodiments of the present invention, when the tablet is formed, the compression pressure may be in the range of approximately 200 kgf to 900 kgf, preferably approximately 300 kgf to 800 kgf, and more preferably approximately 400 kgf to 600 kgf.

In one exemplary embodiment of the present invention, the granules may be manufactured by a wet granulation. That is, a binder may be added to the mixture to prepare the wet granule. No particular limitations are imported on the binder. The binder may be liquid, and preferably, the binder may be a solution of hydroxypropyl cellulose in water, or a solution of hydroxypropylmethyl cellulose in water and preferably the solution of hydroxypropyl cellulose in water.

In another exemplary embodiment of the present invention, the granules may be manufactured by a dry granulation.

According to the present invention, the pharmaceutically acceptable salt may be a metal salt of fimasartan, preferably an alkali metal salt, and more preferably fimasartan potassium.

According to the present invention, the hydrate may be a hydrate of the pharmaceutically acceptable salt of fimasartan. The hydrate may be a hydrate of fimasartan potassium, preferably fimasartan potassium monohydrate or fimasartan potassium trihydrate, and more preferably fimasartan potassium trihydrate.

According to the present invention, the active ingredient contained in the tablet may be fimasartan potassium monohydrate or fimasartan potassium trihydrate and preferably fimasartan potassium trihydrate.

According to the present invention, the tablet may be an uncoated tablet, a coated tablet or a double layered tablet. Preferably, the tablet may be the coated tablet.

In accordance with a further aspect thereof, the present invention provides a tablet comprising fimasartan, a pharmaceutically acceptable salt thereof, or a hydrate or solvate thereof as an active ingredient, and pharmaceutically acceptable additives. In the tablet, 50% (v/v) of the active ingredient based on the total amount of the active ingredient is particles having a diameter of 10 μm or less.

According to the present invention, 90% (v/v) of the active ingredient based on the total amount of the active ingredient, which is fimasartan, a pharmaceutically acceptable salt thereof, or a hydrate or solvate thereof contained in the tablet is a particle having a diameter of 25 μm or less.

According to the present invention, 90% (v/v) of the active ingredient based on the total amount of the active ingredient which is fimasartan, a pharmaceutically acceptable salt thereof, or a hydrate or solvate thereof contained in the tablet is a particle having a diameter of 25 μm or less, and 50% (v/v) of the active ingredient based on the total amount of the active ingredient have diameter of 10 μm or less.

According to the present invention, 50% (v/v) of the active ingredient based on the total amount of the active ingredient, which is fimasartan, a pharmaceutically acceptable salt thereof, or a hydrate or solvate thereof contained in the tablet, have a diameter of 6 μm or less.

According to the present invention, 90% (v/v) of the active ingredient based on the total amount of the active ingredient, which is fimasartan, a pharmaceutically acceptable salt thereof, or a hydrate or solvate thereof contained in the tablet, have a diameter of 15 μm or less.

According to the present invention, 90% (v/v) of the active ingredient based on the total amount of the active ingredient which is fimasartan, a pharmaceutically acceptable salt thereof, or a hydrate or solvate thereof contained in the tablet, have a diameter of 15 μm or less and 50% (v/v) of the active ingredient based on the total amount of the active ingredient have a diameter of 6 μm or less.

According to the present invention, the pharmaceutically acceptable additives may include lactose, lactose hydrate, dextrose, sucrose, sorbitol, mannitol, xylitol, erythritol, maltitol, starch, corn starch, acacia gum, alginate, gelatin, calcium phosphate, calcium silicate, cellulose, methyl cellulose, ethyl cellulose, microcrystalline cellulose, polyvinyl pyrrolidone, crospovidone, sodium starch glycolate, hydroxypropylcellulose, hydroxypropylmethylcellulose, hydroxyethylcellulose, methyl hydroxybenzoate, propyl hydroxybenzoate, talc, croscarmellose sodium, magnesium stearate, mineral oil, or a mixture thereof, with preference for lactose, lactose hydrate, microcrystalline cellulose, croscarmellose sodium, magnesium stearate, or a mixture thereof.

In one exemplary embodiment of the present invention, the active ingredient, which is fimasartan, a pharmaceutically acceptable salt thereof, or a hydrate or solvate thereof, is the particles having a diameter of 0.5 μm or more.

In another exemplary embodiment of the present invention, the active ingredient which is fimasartan, a pharmaceutically acceptable salt thereof, or a hydrate or solvate thereof, is the particle having a diameter of 2 μm or larger and preferably 3 μm or more.

In another exemplary embodiment of the present invention, the active ingredient contained in the tablet may be a hydrate of fimasartan potassium, and preferably fimasartan potassium trihydrate.

According to the present invention, the tablet may be an uncoated tablet, a coated tablet or a double layered tablet. Preferably, the tablet may be the coated tablet.

Advantageous Effects of Invention

The present invention provides the method of preparing the tablet including fimasartan, a pharmaceutically acceptable salt thereof, or a hydrate or solvate thereof as the active ingredient. The tablet of the present invention is prepared using the particle of the active ingredient having a specific particle size distribution by milling the active ingredient to improve the compressibility of the mixture including the active ingredient. As a result, the hardness of the tablet may be increased with an increase in the compression pressure the disintegration time may be easily controlled and friability of the tablet may be decreased.

MODE FOR THE INVENTION

A better understanding of the present invention may be obtained through the following examples which are set forth to illustrate, but are not to be construed as limiting the present invention. Unless stated otherwise, the reagents and materials used in Examples were purchased from Sigma-Aldrich Korea.

Preparation Example 1

Using a jet mill (JE-12, JE Powder), fimasartan potassium trihydrate (Boryung Pharmaceuticals) was milled to give particles having a size distribution of D50=1.7 μm and D90=5.0 μm (Refer FIG. 1). That is, a maximum particle diameter was 1.7 μm in 50% (v/v) of fimasartan potassium trihydrate based on the total amount of fimasartan potassium trihydrate and a maximum particle diameter was 5.0 μm in 90% (v/v) of fimasartan potassium trihydrate based on the total amount of fimasartan potassium trihydrate. Particle sizes were measured using a laser diffraction particle size analyzer (Sympatec, HELOS system).

Preparation Example 2

Using a jet mill (JE-12, JE Powder), fimasartan potassium trihydrate (Boryung Pharmaceuticals) was milled to give particles having a size distribution of D50=2.9 µm and D90=11.2 µm (Refer FIG. 1). That is, a maximum particle diameter was a 2.9 µm in 50% (v/v) of fimasartan potassium trihydrate based on the total amount of fimasartan potassium trihydrate and a maximum particle diameter was 11.2 µm in 90% (v/v) of fimasartan potassium trihydrate based on the total amount of fimasartan potassium trihydrate. Particle sizes were measured using a laser diffraction particle size analyzer (Sympatec, HELOS system).

Preparation Example 3

Using a jet mill (JE-12, JE Powder), fimasartan potassium trihydrate (Boryung Pharmaceuticals) was milled to give particles having a size distribution of D50=3.7 µm and D90=11.4 µm (Refer FIG. 1). That is, a maximum particle diameter was a 3.7 µm in 50% (v/v) of fimasartan potassium trihydrate based on the total amount of fimasartan potassium trihydrate and a maximum particle diameter was 11.4 µm in 90% (v/v) of fimasartan potassium trihydrate based on the total amount of fimasartan potassium trihydrate. Particle sizes were measured using a laser diffraction particle size analyzer (Sympatec, HELOS system).

Preparation Example 4

Using a jet mill (JE-12, JE Powder), fimasartan potassium trihydrate (Boryung Pharmaceuticals) was milled to give particles having a size distribution of D50=5.3 µm and D90=13.6 µm (Refer FIG. 1). That is, a maximum particle diameter was a 5.3 µm in 50% (v/v) of fimasartan potassium trihydrate based on the total amount of fimasartan potassium trihydrate and a maximum particle diameter was 13.6 µm in 90% (v/v) of fimasartan potassium trihydrate based on the total amount of fimasartan potassium trihydrate. Particle sizes were measured using a laser diffraction particle size analyzer (Sympatec, HELOS system).

Preparation Example 5

Using a jet mill (JE-12, JE Powder), fimasartan potassium trihydrate (Boryung Pharmaceuticals) was milled to give particles having a size distribution of D50=7.3 µm and D90=22.6 µm (Refer FIG. 1). That is, a maximum particle diameter was a 7.3 µm in 50% (v/v) of fimasartan potassium trihydrate based on the total amount of fimasartan potassium trihydrate and a maximum particle diameter was 22.6 µm in 90% (v/v) of fimasartan potassium trihydrate based on the total amount of fimasartan potassium trihydrate. Particle sizes were measured using a laser diffraction particle size analyzer (Sympatec, HELOS system).

Preparation Example 6

Using a jet mill (JE-12, JE Powder), fimasartan potassium trihydrate (Boryung Pharmaceuticals) was milled to give particles having a size distribution of D50=12.1 µm and D90=37.3 µm (Refer FIG. 1). That is, a maximum particle diameter was a 12.1 µm in 50% (v/v) of fimasartan potassium trihydrate based on the total amount of fimasartan potassium trihydrate and a maximum particle diameter was 37.3 µm in 90% (v/v) of fimasartan potassium trihydrate based on the total amount of fimasartan potassium trihydrate. Particle sizes were measured using a laser diffraction particle size analyzer (Sympatec, HELOS system).

Preparation Example 7

Using a jet mill (JE-12, JE Powder), fimasartan potassium trihydrate (Boryung Pharmaceuticals) was milled to give particles having a size distribution of D50=15.2 µm and D90=69.0 µm (Refer FIG. 1). That is, a maximum particle diameter was a 15.2 µm in 50% (v/v) of fimasartan potassium trihydrate based on the total amount of fimasartan potassium trihydrate and a maximum particle diameter was 69.0 µm in 90% (v/v) of fimasartan potassium trihydrate based on the total amount of fimasartan potassium trihydrate. Particle sizes were measures using a laser diffraction particle size analyzer (Sympatec, HELOS system).

Preparation Example 8

Using a jet mill (JE-12, JE Powder), fimasartan potassium trihydrate (Boryung Pharmaceuticals) was slightly milled to give particles. Then, the particles were allowed to pass through a standard 170 mesh sieve (sieve size 90 µm, KS No. 170) in order that the selected particles had a size distribution of D50=37.8 µm and D90=134.96 µm (Refer FIG. 1). That is, a maximum particle diameter was a 37.8 µm in 50% (v/v) of fimasartan potassium trihydrate based on the total amount of fimasartan potassium trihydrate and a maximum particle diameter was 134.96 µm in 90% (v/v) of fimasartan potassium trihydrate based on the total amount of fimasartan potassium trihydrate. Particle sizes were measured using a laser diffraction particle size analyzer (Sympatec, HELOS system).

The distributions of the particle size are table 1 below:

TABLE 1

Particle size distribution of Preparation Examples 1 to 8

| | PREPARATION EXAMPLEs | | | | | | | |
|---|---|---|---|---|---|---|---|---|
| | 1 | 2 | 3 | 4 | 5 | 6 | 7 | 8 |
| D50 | 1.7 | 2.9 | 3.7 | 5.3 | 7.3 | 12.1 | 15.2 | 37.8 |
| D90 | 5.0 | 11.2 | 11.4 | 13.6 | 22.6 | 37.3 | 69.0 | 134.9 |

(unit: µm)

Example 1

In a fluidized bed granulator (GPCG-1, Glatt, Germany), 43 mg of fimasartan potassium trihydrate of Preparation Example 1, 29 mg of lactose monohydrate, 7 mg of microcrystalline cellulose, and 15 mg of croscamellose sodium were mixed, with compressed air of 55° C. fed at a rate of 3 m$^3$/min to the granulator to form a mixture.

Separately, a liquid binder was prepared by dissolving 2 mg of hydroxypropyl cellulose in 25 mg of pure water. The liquid binder was sprayed at a rate of 26 g/min over the mixture, followed by manufacturing granules. The granules were dried in the fluidized bed granulator while a compressed air of 85° C. was fed at a rate of 3 m$^3$/min to the granulator.

The resulting granules were mixed with 1.5 mg of magnesium stearate, and compressed at a compression pressure of 300 kgf to prepare an uncoated tablet. The uncoated tablet was then coated with Opadry to afford a coated tablet.

Example 2

With the exception that the compression was carried out at a compression pressure of 500 kgf, a coated tablet was prepared as the same procedure as in Example 1.

Example 3

With the exception that the compression was carried out at a compression pressure of 800 kgf, a coated tablet was prepared as the same procedure as in Example 1.

Example 4

With the exception that the fimasartan potassium trihydrate particles of Preparation Example 2 were used, a coated tablet was prepared in the same procedure as in Example 1.

Example 5

A tablet was prepared in the same procedure as in Example 1, with the exception that the fimasartan potassium trihydrate particles of Preparation Example 2 were used and that the compression was carried out at a compression pressure of 500 kgf.

Example 6

A tablet was prepared in the same procedure as in Example 1, with the exception that the fimasartan potassium trihydrate particles of Preparation Example 2 were used and that the compression was carried out at a compression pressure of 800 kgf.

Example 7

With the exception that the fimasartan potassium trihydrate particles of Preparation Example 3 were used, a coated tablet was prepared in the same procedure as in Example 1.

Example 8

A tablet was prepared in the same procedure as in Example 1, with the exception that the fimasartan potassium trihydrate particles of Preparation Example 3 were used and that the compression was carried out at a compression pressure of 500 kgf.

Example 9

A tablet was prepared in the same procedure as in Example 1, with the exception that the fimasartan potassium trihydrate particles of Preparation Example 3 were used and that the compression was carried out at a compression pressure of 800 kgf.

Example 10

With the exception that the fimasartan potassium trihydrate particles of Preparation Example 4 were used, a coated tablet was prepared in the same procedure as in Example 1.

Example 11

A tablet was prepared in the same procedure as in Example 1, with the exception that the fimasartan potassium trihydrate particles of Preparation Example 4 were used and that the compression was carried out at a compression pressure of 500 kgf.

Example 12

A tablet was prepared in the same procedure as in Example 1, with the exception that the fimasartan potassium trihydrate particles of Preparation Example 4 were used and that the compression was carried out at a compression pressure of 800 kgf.

Example 13

With the exception that the fimasartan potassium trihydrate particles of Preparation Example 5 were used, a coated tablet was prepared in the same procedure as in Example 1.

Example 14

A tablet was prepared in the same procedure as in Example 1, with the exception that the fimasartan potassium trihydrate particles of Preparation Example 5 were used and that the compression was carried out at a compression pressure of 500 kgf.

Example 15

A tablet was prepared in the same procedure as in Example 1, with the exception that the fimasartan potassium trihydrate particles of Preparation Example 5 were used and that the compression was carried out at a compression pressure of 800 kgf.

Comparative Example 1

With the exception that the fimasartan potassium trihydrate particles of Preparation Example 6 were used, a coated tablet was prepared in the same procedure as in Example 1.

Comparative Example 2

A tablet was prepared in the same procedure as in Example 1, with the exception that the fimasartan potassium trihydrate particles of Preparation Example 6 was used and that the compression was carried out at a compression pressure of 500 kgf.

Comparative Example 3

A tablet was prepared in the same procedure as in Example 1, with the exception that the fimasartan potassium trihydrate particles of Preparation Example 6 were used and that the compression was carried out at a compression pressure of 800 kgf.

Comparative Example 4

With the exception that the fimasartan potassium trihydrate particles of Preparation Example 7 were used, a coated tablet was prepared in the same procedure as in Example 1.

Comparative Example 5

A tablet was prepared in the same procedure as in Example 1, with the exception that the fimasartan potassium trihydrate particles of Preparation Example 7 were used and that the compression was carried out at a compression pressure of 500 kgf.

Comparative Example 6

A tablet was prepared in the same procedure as in Example 1, with the exception that the fimasartan potassium trihydrate particles of Preparation Example 7 were used and that the compression was carried out at a compression pressure of 800 kgf.

Comparative Example 7

With the exception that the fimasartan potassium trihydrate particles of Preparation Example 8 were used, a coated tablet was prepared in the same procedure as in Example 1.

Comparative Example 8

A tablet was prepared in the same procedure as in Example 1, with the exception that the fimasartan potassium trihydrate particles of Preparation Example 8 were used and that the compression was carried out at a compression pressure of 500 kgf.

Comparative Example 9

A tablet was prepared in the same procedure as in Example 1, with the exception that the fimasartan potassium trihydrate particles of Preparation Example 8 were used and that the compression was carried out at a compression pressure of 800 kgf.

Comparative Example 10

A tablet was prepared in the same procedure as in Example 1, with the exception that fimasartan potassium trihydrate was not used and 72 mg of lactose monohydrate was used.

Test Example 1

Tablets prepared in the Examples 1 to 15 and the Comparative Examples 1 to 9 were assayed for hardness, disintegration time, and friability. Hardness was measured according to Chapter 1217 (Tablet Breaking Force) of the United States Pharmacopeia (USP). For the analysis procedure of disintegration time, reference was made to Chapter 701 (Disintegration), USP. Friability was calculated according to the following equation after a friability test was performed according to Chapter 1216 (Tablet Friability), USP.

Friability (%)={(Weight (mg) of 20 initial tablets Weight (mg) of 20 tablets post friability test)/ Weight (mg) of 20 initial tablets}×100(%)

Results are summarized in Table 2 below.

TABLE 2

Assay for Hardness, Disintegration Time and Friability of Tablets of Examples 1 to 15 and Comparative Examples 1 to 9

| Examples | Preparation Example | Compression Pressure (kgf) | Hardness (kp) | Disintegration Time (min) | Friability (%) |
|---|---|---|---|---|---|
| Example 1 | Preparation Example 1 | 300 | 8.1 | 3.75 | 1.6 |
| Example 2 | | 500 | 13.5 | 5.33 | 0.3 |
| Example 3 | | 800 | 16.1 | 8.67 | 0.1 |
| Example 4 | Preparation Example 2 | 300 | 7.3 | 3.25 | 1.7 |
| Example 5 | | 500 | 12.1 | 4.92 | 0.2 |
| Example 6 | | 800 | 14.6 | 9.17 | 0.2 |
| Example 7 | Preparation Example 3 | 300 | 6.5 | 2.50 | 1.7 |
| Example 8 | | 500 | 10.9 | 4.83 | 0.4 |
| Example 9 | | 800 | 14.2 | 8.75 | 0.3 |
| Example 10 | Preparation Example 4 | 300 | 6.4 | 2.50 | 1.7 |
| Example 11 | | 500 | 10.8 | 4.83 | 0.4 |

TABLE 2-continued

Assay for Hardness, Disintegration Time and Friability of Tablets of Examples 1 to 15 and Comparative Examples 1 to 9

| Examples | Preparation Example | Compression Pressure (kgf) | Hardness (kp) | Disintegration Time (min) | Friability (%) |
|---|---|---|---|---|---|
| Example 12 | | 800 | 13.8 | 8.50 | 0.4 |
| Example 13 | Preparation Example 5 | 300 | 5.8 | 2.33 | 2.2 |
| Example 14 | | 500 | 9.2 | 4.50 | 0.5 |
| Example 15 | | 800 | 11.8 | 7.75 | 0.4 |
| Comparative Example 1 | Preparation Example 6 | 300 | 3.2 | 1.25 | 2.4 |
| Comparative Example 2 | | 500 | 9.2 | 4.50 | 0.5 |
| Comparative Example 3 | | 800 | 11.8 | 7.75 | 0.4 |
| Comparative Example 4 | Preparation Example 7 | 300 | 2.8 | 0.83 | 3.7 |
| Comparative Example 5 | | 500 | 6.3 | 2.17 | 1.9 |
| Comparative Example 6 | | 800 | 6.7 | 2.42 | 1.8 |
| Comparative Example 7 | Preparation Example 8 | 300 | 2.2 | 0.58 | 4.2 |
| Comparative Example 8 | | 500 | 5.0 | 1.67 | 2.3 |
| Comparative Example 9 | | 800 | 5.1 | 1.92 | 2.2 |

As is clearly understood from data of Table 2, the tablets tended to increase in hardness with an increase in compression pressure when the active ingredient particles had a D50 of 10 μm or less (a maximum particle diameter of 10 μm or less in 50% (v/v) of the active ingredient based on the total amount of the active ingredient) and a D90 of 25 μm or less (a maximum particle diameter of 25 μm or less in 90% (v/v) of the active ingredient based on the total amount of the active ingredient).

In contrast, the tablets of the Comparative Examples did not significantly increase in hardness although compressed at increased compression pressures. For example, even at a compression pressure of 800 kgf, the tablets of the Comparative Examples were found to have a hardness of approximately 7 kp or less, which was similar to the hardness of the tablets of Examples compressed at a compression pressure of 300 kgf.

It is thus understood from the results that when the active ingredient in the tablet has the specific particle size distribution which is a D50 of 10 μm or less and a D90 of 25 μm or less, the fimasartan potassium trihydrate particles can be of high compressibility so that they can be more greatly compressed with an increase in compression pressure, which makes it possible to easily control the hardness and disintegration time of the tablet and to decrease the friability of the tablet to 1% or less. Hence, the method of the present invention allows tablets to be homogeneous in physical properties even in mass production.

To the contrary, as shown in Comparative Examples, when the fimasartan potassium trihydrate has a particle size distribution of a D50 greater than 10 μm and a D90 greater than 25 μm, their compressibility is poor, making it difficult to manufacture a tablet having sufficient hardness even at a high compression pressure. With such a particle size distribution of the active ingredient particles, there is difficulty in controlling the hardness and disintegration time of the tablet, and decreasing friability to 1%. As a result, non-uniform physical properties were detected over the tablets manufactured on a mass scale, thus degrading the product quality.

Test Example 2

Granules prepared in the Examples and the Comparative Examples were assayed for density and Can's index. Density was measured according to Chapter 616 in General Chapter (Bulk density and Tapped density of powders) of the United States Pharmacopeia (USP). Carr's index was calculated according to the following equation:

Carr's index=100×{1(Bulk density/Tapped density)}

Results are summarized in Tables 3, below.

TABLE 3

Assay for Density and Carr's index of Granules of Examples and Comparative Examples

| Examples | Preparation Example | Properties of granules | | |
|---|---|---|---|---|
| | | Bulk Density (g/mL) | Tapped Density (g/mL) | Carr's index |
| Example 1 | Preparation Example 1 | 0.381 | 0.520 | 26.7 |
| Example 4 | Preparation Example 2 | 0.379 | 0.516 | 26.6 |
| Example 7 | Preparation Example 3 | 0.381 | 0.515 | 26.0 |
| Example 10 | Preparation Example 4 | 0.380 | 0.517 | 26.5 |
| Example 13 | Preparation Example 5 | 0.382 | 0.515 | 25.8 |
| Comparative Example 1 | Preparation Example 6 | 0.401 | 0.503 | 20.3 |
| Comparative Example 4 | Preparation Example 7 | 0.403 | 0.495 | 18.6 |
| Comparative Example 7 | Preparation Example 8 | 0.409 | 0.482 | 15.1 |
| Comparative Example 10 | — | 0.469 | 0.532 | 11.8 |

As is clearly understood from data of Table 3, the granules has higher Carr's index when the active ingredient particles had a D50 of 10 μm or less (a maximum particle diameter of 10 μm or less in 50% (v/v) of the active ingredient based on the total amount of the active ingredient) and a D90 of 25 μm or less (a maximum particle diameter of 25 μm or less in 90% (v/v) of the active ingredient based on the total amount of the active ingredient) compared to those of the active ingredients having the D50 value of exceeds 10 μm.

When the Carr's index is increased, the compressibility is increased. Thus, it is confirmed that the granules including the fimasartan potassium hydrate having a D50 of 10 μm or less and a D90 of 25 μm or less superior compressibility.

Example 16

A tablet was prepared in the same procedure as in Example 1, with the exception that 29 mg of D mannitol was used instead of lactose monohydrate and that the compression was carried out at a compression pressure of 500 kgf.

Example 17

With the exception that the compression was carried out at a compression pressure of 800 kgf, a coated tablet was prepared as the same procedure as in Example 16.

Example 18

With the exception that the fimasartan potassium trihydrate particles of Preparation Example 2 were used, a coated tablet was prepared in the same procedure as in Example 16.

Example 19

A tablet was prepared in the same procedure as in Example 16, with the exception that the fimasartan potassium trihydrate particles of Preparation Example 2 were used and that the compression was carried out at a compression pressure of 800 kgf.

Example 20

With the exception that the fimasartan potassium trihydrate particles of Preparation Example 3 were used, a coated tablet was prepared in the same procedure as in Example 16.

Example 21

A tablet was prepared in the same procedure as in Example 16, with the exception that the fimasartan potassium trihydrate particles of Preparation Example 3 were used and that the compression was carried out at a compression pressure of 800 kgf.

Example 22

With the exception that the fimasartan potassium trihydrate particles of Preparation Example 4 were used, a coated tablet was prepared in the same procedure as in Example 16.

Example 23

A tablet was prepared in the same procedure as in Example 16, with the exception that the fimasartan potassium trihydrate particles of Preparation Example 4 were used and that the compression was carried out at a compression pressure of 800 kgf.

Example 24

With the exception that the fimasartan potassium trihydrate particles of Preparation Example 5 were used, a coated tablet was prepared in the same procedure as in Example 16.

Example 25

A tablet was prepared in the same procedure as in Example 16, with the exception that the fimasartan potassium trihydrate particles of Preparation Example 5 were used and that the compression was carried out at a compression pressure of 800 kgf.

Comparative Example 11

With the exception that the fimasartan potassium trihydrate particles of Preparation Example 6 were used, a coated tablet was prepared in the same procedure as in Example 16.

Comparative Example 12

A tablet was prepared in the same procedure as in Example 16, with the exception that the fimasartan potassium trihydrate particles of Preparation Example 6 were used and that the compression was carried out at a compression pressure of 800 kgf.

Comparative Example 13

With the exception that the fimasartan potassium trihydrate particles of Preparation Example 7 were used, a coated tablet was prepared in the same procedure as in Example 16.

Comparative Example 14

A tablet was prepared in the same procedure as in Example 16, with the exception that the fimasartan potassium trihydrate particles of Preparation Example 7 were used and that the compression was carried out at a compression pressure of 800 kgf.

Comparative Example 15

With the exception that the fimasartan potassium trihydrate particles of Preparation Example 8 were used, a coated tablet was prepared in the same procedure as in Example 16.

Comparative Example 16

A tablet was prepared in the same procedure as in Example 16, with the exception that the fimasartan potassium trihydrate particles of Preparation Example 8 were used and that the compression was carried out at a compression pressure of 800 kgf.

Test Example 3

Tablets prepared in the Examples 16 to 25 and the Comparative Examples 11 to 16 were assayed for hardness, disintegration time, and friability the same as those of TEST EXAMPLE 1.

TABLE 4

Assay for Hardness, Disintegration Time and Friability of Tablets of Examples 16 to 25 and Comparative Examples 11 to 16

| Examples | Preparation Example | Compression Pressure (kgf) | Hardness (kp) | Disintegration Time (min) | Friability (%) |
|---|---|---|---|---|---|
| Example 16 | Preparation | 500 | 13.2 | 3.50 | 0.2 |
| Example 17 | Example 1 | 800 | 15.9 | 5.25 | 0.1 |
| Example 18 | Preparation | 500 | 12.0 | 3.25 | 0.3 |
| Example 19 | Example 2 | 800 | 14.6 | 5.00 | 0.1 |
| Example 20 | Preparation | 500 | 11.2 | 3.17 | 0.2 |
| Example 21 | Example 3 | 800 | 14.1 | 4.83 | 0.1 |
| Example 22 | Preparation | 500 | 10.6 | 3.00 | 0.3 |
| Example 23 | Example 4 | 800 | 13.6 | 4.50 | 0.2 |
| Example 24 | Preparation | 500 | 9.6 | 2.83 | 0.3 |
| Example 25 | Example 5 | 800 | 11.4 | 4.00 | 0.2 |
| Comparative Example 11 | Preparation Example 6 | 500 | 6.3 | 1.67 | 1.6 |
| Comparative Example 12 | | 800 | 7.1 | 2.00 | 1.4 |
| Comparative Example 13 | Preparation Example 7 | 500 | 6.1 | 1.33 | 2.5 |
| Comparative Example 14 | | 800 | 6.5 | 1.50 | 2.3 |
| Comparative Example 15 | Preparation Example 8 | 500 | 5.0 | 1.67 | 3.1 |
| Comparative Example 16 | | 800 | 5.1 | 1.00 | 3.0 |

Example 26

A tablet was prepared in the same procedure as in Example 1, with the exception that 29 mg of corn starch was used instead of lactose monohydrate and that the compression was carried out at a compression pressure of 500 kgf.

Example 27

With the exception that the compression was carried out at a compression pressure of 800 kgf, a coated tablet was prepared as the same procedure as in Example 26.

Example 28

With the exception that the fimasartan potassium trihydrate particles of Preparation Example 2 were used, a coated tablet was prepared in the same procedure as in Example 26.

Example 29

A tablet was prepared in the same procedure as in Example 26, with the exception that the fimasartan potassium trihydrate particles of Preparation Example 2 were used and that the compression was carried out at a compression pressure of 800 kgf.

Example 30

With the exception that the fimasartan potassium trihydrate particles of Preparation Example 3 were used, a coated tablet was prepared in the same procedure as in Example 26.

Example 31

A tablet was prepared in the same procedure as in Example 26, with the exception that the fimasartan potassium trihydrate particles of Preparation Example 3 were used and that the compression was carried out at a compression pressure of 800 kgf.

Example 32

With the exception that the fimasartan potassium trihydrate particles of Preparation Example 4 were used, a coated tablet was prepared in the same procedure as in Example 26.

Example 33

A tablet was prepared in the same procedure as in Example 26, with the exception that the fimasartan potassium trihydrate particles of Preparation Example 4 were used and that the compression was carried out at a compression pressure of 800 kgf.

Example 34

With the exception that the fimasartan potassium trihydrate particles of Preparation Example 5 were used, a coated tablet was prepared in the same procedure as in Example 26.

Example 35

A tablet was prepared in the same procedure as in Example 26, with the exception that the fimasartan potassium trihydrate particles of Preparation Example 5 were used and that the compression was carried out at a compression pressure of 800 kgf.

Comparative Example 17

With the exception that the fimasartan potassium trihydrate particles of Preparation Example 6 were used, a coated tablet was prepared in the same procedure as in Example 26.

Comparative Example 18

A tablet was prepared in the same procedure as in Example 26, with the exception that the fimasartan potassium trihydrate particles of Preparation Example 6 were used and that the compression was carried out at a compression pressure of 800 kgf.

Comparative Example 19

With the exception that the fimasartan potassium trihydrate particles of Preparation Example 7 were used, a coated tablet was prepared in the same procedure as in Example 26.

Comparative Example 20

A tablet was prepared in the same procedure as in Example 26, with the exception that the fimasartan potassium trihydrate particles of Preparation Example 7 were used and that the compression was carried out at a compression pressure of 800 kgf.

Comparative Example 21

With the exception that the fimasartan potassium trihydrate particles of Preparation Example 8 were used, a coated tablet was prepared in the same procedure as in Example 26.

Comparative Example 22

A tablet was prepared in the same procedure as in Example 26, with the exception that the fimasartan potassium trihydrate particles of Preparation Example 8 were used and that the compression was carried out at a compression pressure of 800 kgf.

Test Example 4

Tablets prepared in the Examples 26 to 35 and the Comparative Examples 17 to 22 were assayed for hardness, disintegration time, and friability the same as those of TEST EXAMPLE 1.
Results are summarized in Table 5 below.

TABLE 5

Assay for Hardness, Disintegration Time and Friability of Tablets of Examples 26 to 35 and Comparative Examples 17 to 22

| Examples | Preparation Example | Compression Pressure (kgf) | Hardness (kp) | Disintegration Time (min) | Friability (%) |
|---|---|---|---|---|---|
| Example 26 | Preparation Example 1 | 500 | 13.5 | 5.67 | 0.1 |
| Example 27 | | 800 | 16.3 | 8.83 | 0.1 |
| Example 28 | Preparation Example 2 | 500 | 12.3 | 5.33 | 0.2 |
| Example 29 | | 800 | 14.9 | 8.67 | 0.2 |
| Example 30 | Preparation Example 3 | 500 | 11.6 | 5.17 | 0.2 |
| Example 31 | | 800 | 14.5 | 8.25 | 0.1 |
| Example 32 | Preparation Example 4 | 500 | 10.2 | 4.83 | 0.2 |
| Example 33 | | 800 | 13.2 | 7.83 | 0.1 |
| Example 34 | Preparation Example 5 | 500 | 9.3 | 4.75 | 0.2 |
| Example 35 | | 800 | 11.4 | 7.67 | 0.1 |
| Comparative Example 17 | Preparation Example 6 | 500 | 6.8 | 2.83 | 1.5 |
| Comparative Example 18 | | 800 | 6.9 | 3.00 | 1.2 |
| Comparative Example 19 | Preparation Example 7 | 500 | 6.4 | 2.25 | 2.1 |
| Comparative Example 20 | | 800 | 6.8 | 2.75 | 2.1 |
| Comparative Example 21 | Preparation Example 8 | 500 | 5.2 | 1.67 | 2.6 |
| Comparative Example 22 | | 800 | 5.4 | 1.25 | 2.4 |

Example 36

A tablet was prepared in the same procedure as in Example 1, with the exception that 2.0 mg of hydroxypropylmethyl cellulose was used instead of hydroxypropyl cellulose and that the compression was carried out at a compression pressure of 500 kgf.

Example 37

With the exception that the compression was carried out at a compression pressure of 800 kgf, a coated tablet was prepared as the same procedure as in Example 36.

Example 38

With the exception that the fimasartan potassium trihydrate particles of Preparation Example 2 were used, a coated tablet was prepared in the same procedure as in Example 36.

Example 39

A tablet was prepared in the same procedure as in Example 36, with the exception that the fimasartan potassium trihydrate particles of Preparation Example 2 were used and that the compression was carried out at a compression pressure of 800 kgf.

Example 40

With the exception that the fimasartan potassium trihydrate particles of Preparation Example 3 were used, a coated tablet was prepared in the same procedure as in Example 36.

Example 41

A tablet was prepared in the same procedure as in Example 36, with the exception that the fimasartan potassium trihydrate particles of Preparation Example 3 were used and that the compression was carried out at a compression pressure of 800 kgf.

Example 42

With the exception that the fimasartan potassium trihydrate particles of Preparation Example 4 were used, a coated tablet was prepared in the same procedure as in Example 36.

Example 43

A tablet was prepared in the same procedure as in Example 36, with the exception that the fimasartan potassium trihydrate particles of Preparation Example 4 were used and that the compression was carried out at a compression pressure of 800 kgf.

Example 44

With the exception that the fimasartan potassium trihydrate particles of Preparation Example 5 were used, a coated tablet was prepared in the same procedure as in Example 36.

Example 45

A tablet was prepared in the same procedure as in Example 36, with the exception that the fimasartan potassium trihydrate particles of Preparation Example 5 were used and that the compression was carried out at a compression pressure of 800 kgf.

Comparative Example 23

With the exception that the fimasartan potassium trihydrate particles of Preparation Example 6 were used, a coated tablet was prepared in the same procedure as in Example 36.

Comparative Example 24

A tablet was prepared in the same procedure as in Example 36, with the exception that the fimasartan potassium trihydrate particles of Preparation Example 6 were used and that the compression was carried out at a compression pressure of 800 kgf.

Comparative Example 25

With the exception that the fimasartan potassium trihydrate particles of Preparation Example 7 were used, a coated tablet was prepared in the same procedure as in Example 36.

Comparative Example 26

A tablet was prepared in the same procedure as in Example 36, with the exception that the fimasartan potassium trihydrate particles of Preparation Example 7 were used and that the compression was carried out at a compression pressure of 800 kgf.

Comparative Example 27

With the exception that the fimasartan potassium trihydrate particles of Preparation Example 8 were used, a coated tablet was prepared in the same procedure as in Example 36.

Comparative Example 28

A tablet was prepared in the same procedure as in Example 36, with the exception that the fimasartan potassium trihydrate particles of Preparation Example 8 were used and that the compression was carried out at a compression pressure of 800 kgf.

Test Example 5

Tablets prepared in the Examples 36 to 45 and the Comparative Examples 23 to 28 were assayed for hardness, disintegration time, and friability the same as those of TEST EXAMPLE 1.

Results are summarized in Table 6 below.

TABLE 6

Assay for Hardness, Disintegration Time and Friability of Tablets of Examples 36 to 45 and Comparative Examples 23 to 28

| Examples | Preparation Example | Compression Pressure (kgf) | Hardness (kp) | Disintegration Time (min) | Friability (%) |
|---|---|---|---|---|---|
| Example 36 | Preparation Example 1 | 500 | 14.6 | 6.83 | 0.1 |
| Example 37 | | 800 | 18.2 | 10.67 | 0.0 |
| Example 38 | Preparation Example 2 | 500 | 13.6 | 5.67 | 0.0 |
| Example 39 | | 800 | 16.8 | 10.67 | 0.0 |
| Example 40 | Preparation Example 3 | 500 | 12.5 | 5.17 | 0.0 |
| Example 41 | | 800 | 16.2 | 10.00 | 0.0 |
| Example 42 | Preparation Example 4 | 500 | 11.8 | 5.00 | 0.1 |
| Example 43 | | 800 | 15.6 | 9.33 | 0.0 |
| Example 44 | Preparation Example 5 | 500 | 10.5 | 4.75 | 0.1 |
| Example 45 | | 800 | 14.1 | 8.83 | 0.1 |
| Comparative Example 23 | Preparation Example 6 | 500 | 7.2 | 3.25 | 1.1 |
| Comparative Example 24 | | 800 | 7.6 | 3.83 | 1.1 |
| Comparative Example 25 | Preparation Example 7 | 500 | 6.6 | 2.83 | 1.5 |
| Comparative Example 26 | | 800 | 6.9 | 2.83 | 1.4 |
| Comparative Example 27 | Preparation Example 8 | 500 | 5.3 | 2.25 | 2.0 |
| Comparative Example 28 | | 800 | 5.8 | 2.67 | 1.8 |

Comparative Example 29

A tablet was prepared in the same procedure as in Example 1, with the exception that the fimasartan potassium trihydrate was not used, 72 mg of lactose monohydrate was used and the compression was carried out at a compression pressure of 500 kgf.

Comparative Example 30

A tablet was prepared in the same procedure as in Example 1, with the exception that the fimasartan potassium trihydrate was not used, 72 mg of lactose monohydrate was used and the compression was carried out at a compression pressure of 800 kgf.

Test Example 6

Tablets prepared in the Comparative Examples 29 and 30 were assayed for hardness, disintegration time, and friability the same as those of TEST EXAMPLE 1.

Results are summarized in Table 7 below.

TABLE 7

Assay for Hardness, Disintegration Time and Friability of Tablets of Comparative Examples 29 to 30

| Examples | Compression Pressure (kgf) | Hardness (kp) | Disintegration Time (min) | Friability (%) |
|---|---|---|---|---|
| Comparative Example 29 | 500 | 5.8 | 2.75 | 2.4 |
| Comparative Example 30 | 800 | 6.1 | 3.83 | 2.1 |

As is clearly understood from data of Tables 4 to 6, the tablets according to Examples 16 to 45 exhibited superior hardness, disintegration time, and friability to those of comparative Examples 11 to 28 although the additives included in the tablet is changed from lactose monohydrate and hydroxypropyl cellulose into D mannitol (Examples 16 to 25), corn starch (Examples 26 to 35) and hydroxypropylmethyl cellulose (Examples 36 to 45), respectively.

Additionally, as shown in Table 7, when tablet was prepared without the active ingredient of the fimasartan potassium trihydrate, hardness, disintegration time and friability are inferior to those of tablets according to Examples 1 to 45 including the active ingredient of the fimasartan potassium trihydrate.

Thus, it is confirmed that the properties of the tablet are not greatly affected by the additives when the amount of the active ingredients of fimasartan potassium trihydrate is high in the tablet.

What is claimed is:

1. A method for preparing a tablet, comprising:
   milling at least 50% (v/v) of an active ingredient based on the total amount of the active ingredient into particles which have a diameter of 10 μm or less, the active ingredient being fimasartan, a pharmaceutically acceptable salt thereof, or a hydrate or solvate thereof;
   mixing the particles of the milled active ingredient with a pharmaceutically acceptable additive to give a mixture; and
   forming the tablet from the mixture.

2. The method of claim 1, wherein the milling is carried out in such a way that 90% (v/v) of the active ingredient based on the total amount of the active ingredient contained in the tablet is milled into the particles having a diameter of 25 μm or less.

3. The method of claim 1, wherein the milling is carried out in such a way that 90% (v/v) of the active ingredient based on the total amount of the active ingredient contained in the tablet is milled into the particles having a diameter of 15 μm or less and 50% (v/v) of the active ingredient based on the total amount of the active ingredient contained in the tablet is milled into the particles having a diameter of 6 μm or less.

4. The method of claim 1, wherein the milling is carried out in such a way that the active ingredient contained in the tablet is milled into particles having a diameter of 0.5 μm or more.

5. The method of claim 1, wherein the milling is carried out in such a way that the active ingredient contained in the tablet is milled into particles having a diameter of 2 μm or more.

6. The method of claim 1, wherein the milling is carried out in such a way that the active ingredient contained in the tablet is milled into particles with a diameter of 3 μm or more.

7. The method of claim 1, wherein the forming the tablet comprises:
   preparing granules from the mixture;
   adding an additional pharmaceutically acceptable additive to the granule to give a granule-containing mixture; and
   compressing the granule-containing mixture into the tablet.

8. The method of claim 7, wherein the forming the tablet further comprises adding a binder to the mixture before the preparation of granules.

9. The method of claim 1, wherein forming the tablet comprises compressing the mixture into the tablet.

10. The method of claim 1, wherein the active ingredient is a hydrate of fimasartan potassium.

11. The method of claim 1, wherein the active ingredient is fimasartan potassium trihydrate.

12. The method of claim 1, wherein the pharmaceutically acceptable additive is selected from the group consisting of lactose or a hydrate thereof, microcrystalline cellulose, croscarmellose sodium, magnesium stearate and mixture thereof.

13. A tablet, comprising fimasartan, a pharmaceutically acceptable salt thereof, or a hydrate or solvate thereof as an active ingredient, and a pharmaceutically acceptable additive,
   wherein 50% (v/v) of the active ingredient based on the total amount of the active ingredient is a particle having a diameter of 10 μm or less.

14. The tablet of claim 13, wherein 90% (v/v) of the active ingredient based on total amount of the active ingredient is the particles having a diameter of 25 μm or less.

15. The tablet of claim 13, wherein 90% (v/v) of the active ingredient based on total amount of the active ingredient contained in the tablet is the particles having a diameter of 15 μm or less and 50% (v/v) of the active ingredient based on the total amount of the active ingredient is the particles having a diameter of 6 μm or less.

16. The tablet of claim 13, wherein the active ingredient comprises the particles having a diameter of 0.5 μm or more.

17. The tablet of claim 13, wherein the active ingredient comprises the particles having a diameter of 2 μm or more.

18. The tablet of claim 13, wherein the active ingredient comprises the particles having a diameter of 3 μm or more.

19. The tablet of claim 13, wherein the tablet is a coated tablet.

20. The tablet of claim 13, wherein the active ingredient is fimasartan potassium trihydrate.

* * * * *